United States Patent

McMaster et al.

(10) Patent No.: US 6,821,998 B2
(45) Date of Patent: Nov. 23, 2004

(54) ARYLAMINES AS INHIBITORS OF CHEMOKINE BINDING TO US28

(75) Inventors: Brian E. McMaster, Mountain View, CA (US); Thomas J. Schall, Palo Alto, CA (US); Mark Penfold, Mountain View, CA (US); J. J. Wright, Redwood City, CA (US); Daniel J. Dairaghi, Palo Alto, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 10/233,336

(22) Filed: Aug. 29, 2002

(65) Prior Publication Data

US 2003/0114423 A1 Jun. 19, 2003

Related U.S. Application Data

(60) Provisional application No. 60/316,386, filed on Aug. 30, 2001.

(51) Int. Cl.$^7$ .................... A61K 31/40; C07D 207/04; A61P 31/12
(52) U.S. Cl. .................... 514/429; 514/428; 514/645; 548/575; 548/577; 564/304
(58) Field of Search .................... 548/577, 575, 548/967, 954, 530; 564/304; 514/429, 428, 645, 255.03, 254.01, 423, 326, 357, 235.5, 210.01, 183; 546/208, 246; 544/394, 141, 372

(56) References Cited

U.S. PATENT DOCUMENTS

| | | |
|---|---|---|
| 3,272,630 A | 9/1966 | Rauhut and Süs |
| 3,432,301 A | 3/1969 | Rauhut and Süs |
| 5,935,995 A | 8/1999 | Bosslet et al. |
| 6,034,102 A | 3/2000 | Aiello |
| 6,420,121 B1 | 7/2002 | Nelson et al. |
| 2002/0061599 A1 | 5/2002 | Elling et al. |
| 2002/0127544 A1 | 9/2002 | Schall et al. |
| 2002/0193374 A1 | 12/2002 | Schall et al. |

FOREIGN PATENT DOCUMENTS

| | | |
|---|---|---|
| EP | 0 795 334 A2 | 9/1997 |
| NL | 64014808 * | 7/1965 |
| WO | WO 98/02151 A | 1/1998 |
| WO | WO 00/00491 A1 | 1/2000 |
| WO | WO 00/11950 A1 | 3/2000 |
| WO | WO 00/55377 A1 | 9/2000 |
| WO | WO 02/17900 A2 | 3/2002 |
| WO | WO 02/17969 A2 | 3/2002 |
| WO | WO 02/18954 A2 | 3/2002 |

OTHER PUBLICATIONS

Beisser et al., 2002, "Viral Chemokine Receptors and Chemokines in Human Cytomegalovirus Trafficking and Interaction with the Immune System," *Curr. Top. Microbiol. Immunol.* 269:203–234.

Debnath et al., 1999, "Structure–based identification of small molecule antiviral compounds targeted to the gp41 core structure of the human immunodeficiency virus type I," *J. Med. Chem.* 42:3203–3209.

Horuk, R., 1994, "Molecular properties of the chemokine receptor family", *Trends Pharm. Sci.* 15:159–165.

Kledal et al., 1998, "Selective recognition of the membrane–bound CX$_3$C Chemokine, fractalkine, by the human cytomegalovirus–encoded broad–spectrum receptor US28," *FEBS Letters* 441:209–214.

Michelson, S., 1999, "Cytomegalovirus (CMV) and sequenstration of chemokines," *Eur. Cytokine Netw.* 10(2): 286–287.

Schall et al., 1994, "Chemokines, leukocyte trafficking and inflammation," *Curr. Opin. Immunol.* 6:865–873.

Schall, T., 1991, "Biology of the Rantes/SIS Cytokine Family," *Cytokine* 3(3):165–183.

* cited by examiner

*Primary Examiner*—Rita Desai
*Assistant Examiner*—Robert Shiao
(74) *Attorney, Agent, or Firm*—Townsend and Townsend and Crew LLP

(57) ABSTRACT

Methods for treating CMV and CMV-related diseases are provided that use compounds having the formula:

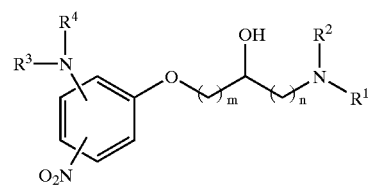

wherein the subscripts m and n are each independently integers from 1 to 2; and the R groups are as defined in the specification.

12 Claims, No Drawings

ARYLAMINES AS INHIBITORS OF CHEMOKINE BINDING TO US28

CROSS-REFERENCES TO RELATED APPLICATIONS

This application claims the benefit of U.S. Provisional Application Ser. No. 60/316,386, filed Aug. 30, 2001, the contents of which are incorporated herein by reference.

STATEMENT AS TO RIGHTS TO INVENTIONS MADE UNDER FEDERALLY SPONSORED RESEARCH OR DEVELOPMENT

The United States government may have certain rights to inventions described herein pursuant to DARPA grant No. N66001-01-C-8009.

BACKGROUND OF THE INVENTION

Cytomegalovirus (CMV) is an important human pathogen and a major opportunist which emerges to cause disease in the immuno-compromised such as AIDS patients, neonates, and individuals who have been given immunosuppressive drugs as part of a transplantation regimen. In these individuals, the consequences of CMV in acute or re-emerging infections can be dire, including retinitis, encephalitis, and pneumocystis, among other pathologies. Furthermore, in immuno-competent hosts, CMV establishes a persistent lifelong infection through which it has been linked to a variety of inflammatory conditions including coronary artery occlusion following heart transplant and atherectomy and restenosis following angioplasty. CMV interacts with leukocytes during acute infection of the host as well as during lifelong latency. As such, leukocytes are important players in CMV-induced disease and have been implicated in the acute phase of infection as vehicles for dissemination of virus and as sites of residence during lifelong latency.

CMV harbors in its genome an open reading frame (ORF), designated US28, which encodes a protein that acts as a functional receptor for certain human and viral chemokines. Upon infection of a cell by CMV, US28 is expressed on the surface of the infected cell and becomes capable of responding to chemokines in the environment. Because the virus on its own is inherently non-motile, and because chemokines and their receptors encoded by human cells are known to regulate the migration of leukocytes and other cells through the body, CMV US28 is thought to be encoded by the virus to facilitate the dissemination of CMV through the body during and after infection. Therefore, agents which block the binding of chemokines to US28 should prove useful in inhibiting viral dissemination during acute or re-emerging CMV infection.

CMV US28 has been shown to bind a variety of human, murine, and virus-encoded CC chemokines in a variety of assay formats. In addition, the CX3C chemokine, Fractalkine, binds with a very high affinity ($K_f$~50 pM) to US28. Fractalkine is expressed on certain endothelial cell surfaces and on populations of dendritic cells (DC), and may thus define a portal through which CMV infected cells go from the circulation to the tissue space, as well as find residence in the DC.

Since the US28 receptor is expressed on cytomegalovirus infected cells, and also in view of its ability to bind multiple chemokines, a small molecule inhibitor for this receptor would have significant use as an anti-CMV agent.

SUMMARY OF THE INVENTION

In one aspect, the present invention provides methods for treating or preventing viral dissemination from CMV infection. The methods typically involve administering to a patient an effective formulation of one or more of the compounds of formula I:

$$Ar\diagdown_{L}\diagup N \diagdown_{R^2}^{R^1} \quad (I)$$

wherein Ar is a substituted or unsubstituted 5–14 membered heteroaryl group having from 1 to 5 heteroatoms as ring members, or a substituted or unsubstituted ($C_6$–$C_{14}$)aryl group; L is a substituted or unsubstituted linkage having from two to fourteen contiguous chain atoms selected from the group consisting of C, N, O, P and S; and $R^1$ and $R^2$ are each independently selected from ($C_1$–$C_4$)alkyl, wherein the alkyl portions of L, $R^1$ and $R^2$ are optionally substituted with from one to four substituents selected from halo, OR', SR', S($O_p$)R', and $CO_2$R', in which R' is H or a ($C_1$–$C_4$)alkyl group, and the subscript p is 1 or 2; or $R^1$ and $R^2$ are optionally combined with the nitrogen atom to which each is attached to form a ring selected from aziridine, azetidine, pyrrolidine, piperidine, imidazoline, piperazine and morpholine, each of the rings being optionally substituted with from one to three substituents selected from ($C_1$–$C_4$) alkyl, phenyl, phenyl($C_1$–$C_4$)alkyl, hydroxy, hydroxy ($C_1$–$C_4$)alkyl, ($C_1$–$C_4$)alkoxy($C_1$–$C_4$)alkyl and di($C_1$–$C_4$) alkylamino) $C_1$–$C_4$)alkyl.

In a group of particularly preferred embodiments, the compounds have the formula:

$$R^3-N(R^4)-\underset{O_2N}{\underset{|}{\text{Ar}}}-O-(CH_2)_m-CH(OH)-(CH_2)_n-N(R^2)-R^1$$

wherein the subscripts m and n are each independently integers from 1 to 2; $R^1$ and $R^2$ are as defined above for formula I; and $R^3$ and $R^4$ are each independently selected from the group consisting of ($C_1$–$C_4$)alkyl, or when taken together with the nitrogen atom to which each is attached, form a ring selected from the group consisting of aziridine, azetidine, pyrrolidine, piperidine, imidazoline, piperazine and morpholine, each of the rings being optionally substituted with from one to three substituents selected from ($C_1$–$C_4$)alkyl, phenyl, phenyl($C_1$–$C_4$)alkyl, hydroxy, hydroxy($C_1$–$C_4$)alkyl, ($C_1$–$C_4$)alkoxy($C_1$–$C_4$)alkyl and di($C_1$–$C_4$)alkylamino($C_1$–$C_4$)alkyl.

Additionally, the invention provides compositions of the above compounds in combination with a pharmaceutically acceptable carrier or excipient.

BRIEF DESCRIPTION OF THE DRAWINGS

None

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An "unsaturated alkyl" group (e.g., an alkenyl or alkynyl group) is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$—$CH_2$—$CH_2$,S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Generally, the aryl groups will have from six to fourteen carbon atoms as ring members, while the heteroaryl groups will have from six to fourteen ring members selected from carbon, nitrogen, sulfur and oxygen. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. When the aryl or heteroaryl groups are provided as being "substituted or unsubstituted" the substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are often noted as "substituted or unsubstituted" and will include substituents for each type of radical as provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NH—C($NH_2$)=NH, —NR'C($NH_2$)=NH, —NH—C($NH_2$) =NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "substituted alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula —T—C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

In related co-owned application Ser. Nos. 09/944,163, 09/944,051 and 09/944,049, all filed Aug. 30, 2001 and incorporated herein by reference, assays for identifying compounds useful for blocking CMV dissemination in a host were provided. Typically, these assays determine whether the compound inhibits the binding of a chemokine to US28 or a US28 fragment, and are run as a competitive binding assay using a labeled chemokine. A variety of chemokines are known to bind to US28 and are useful in such assays. Preferably, the chemokine is fractalkine and the assay is a radioligand binding assay.

Following methods outlined in the above-noted applications, compounds have now been identified that are effective in therapeutic methods involving the blocking of CMV dissemination in a host.

Description of the Embodiments

A. Methods of Treating CMV Infection

In one aspect, the present invention provides novel methods for treating or preventing CMV infection or diseases associated with, or resultant from, CMV infection. Without intending to be bound by theory, it is believed that the compounds and compositions provided below, exert their effect by inhibiting US28-mediated viral dissemination. The methods typically involve administering to a patient an effective formulation of one or more of the subject compounds or compositions described in more detail below (e.g., compounds of formula I).

The invention provides methods of using the compounds and compositions described below to treat disease or provide medicinal prophylaxis to individuals who possess a compromised immune system or are expected to suffer immunosuppressed conditions, such as patients prior to undergoing immunosuppressive therapy in connection with organ transplantation or anticancer chemotherapy. Additional methods are provided for the treatment of CMV-associated diseases (e.g., atherosclerosis or cardiovascular diseases) in non-immunocompromised individuals. These methods generally involve administering to the host an effective amount of the subject compounds or pharmaceutically acceptable compositions.

The compositions and compounds described herein and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Therapeutic and prophylactic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions. Compounds of the invention may also be administered via an intraocular implant for treating retinitis as a result of CMV infection. In particular, compounds may be embedded in a polymer based implant which will be release into the eye over an extended period of time.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

B. Compounds Which Block CMV Dissemination

Compounds that are useful in blocking CMV dissemination have been identified using the assays described below, and have been found to possess a structure of general formula I.

In one group of embodiments, the compounds have the formula I:

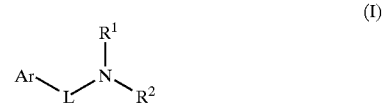

wherein Ar is a substituted or unsubstituted 5–14 membered heteroaryl group or a substituted or unsubstituted ($C_6$–$C_{14}$) aryl group; L is a substituted or unsubstituted linkage having from two to fourteen contiguous chain atoms selected from the group consisting of C, N, O, P and S; and $R^1$ and $R^2$ are each independently selected from the group consisting of ($C_1$–$C_4$)alkyl; wherein any alkyl portions of L, $R^1$ and $R^2$ are optionally substituted with from one to four substituents selected from halo, OR', SR', S(O)$_p$R', and CO$_2$R', in which R' is H or a ($C_1$–$C_4$)alkyl group and the subscript p is an integer of from 1 to 2; or $R^1$ and $R^2$ are optionally combined with the nitrogen atom to which each is attached to form a ring selected from aziridine, azetidine, pyrrolidine, piperidine, imidazoline, piperazine and morpholine, each of the rings being optionally substituted with from one to three substituents selected from ($C_1$–$C_4$)alkyl, phenyl, phenyl($C_1$–$C_4$)alkyl, hydroxy, hydroxy($C_1$–$C_4$)alkyl, ($C_1$–$C_4$)alkoxy($C_1$–$C_4$)alkyl and di($C_1$–$C_4$)alkylamino($C_1$–$C_4$)alkyl.

In preferred embodiments, $R^1$ and $R^2$ are independently selected from methyl, ethyl and n-propyl. More preferably $R^1$ and $R^2$ are both ethyl.

In other preferred embodiments, Ar is a substituted phenyl, substituted benzimidazole, substituted indole, substituted 6,7-benzoquinoline or a substituted 6,7-benzoisoquinoline.

In still other preferred embodiments, L is a linking group selected from —N═C(CH$_3$)—, —NH—CH(CH$_3$)CH$_2$CH$_2$CH$_2$—, —CH$_2$CH$_2$—, —OCH$_2$CH(OH)CH$_2$— and —NHCH$_2$CH$_2$CH$_2$—. More preferably, L is —NH—CH(CH$_3$)CH$_2$CH$_2$CH$_2$—, —CH$_2$CH$_2$—, —OCH$_2$CH(OH)CH$_2$— or —NHCH$_2$CH$_2$CH$_2$—.

In one group of particularly preferred embodiments, L is selected from —N═C(CH$_3$)—, —NH—CH(CH$_3$)CH$_2$CH$_2$CH$_2$—, —CH$_2$CH$_2$—, —OCH$_2$CH(OH)CH$_2$— and —NHCH$_2$CH$_2$CH$_2$—; $R^1$ and $R^2$ are each ethyl; and Ar is a substituted phenyl having the formula:

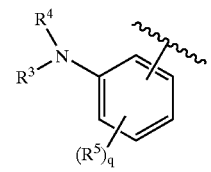

wherein the subscript q is an integer of from 0 to 3; each $R^5$ is a substituent independently selected from halogen, NO$_2$, CN, R, OR, NR$_2$, CO$_2$R, C(O)R, OC(O)R, NRC(O)R and NRC(O)NR$_2$, wherein each R is independently selected from H and ($C_1$–$C_8$)alkyl; and $R^3$ and $R^4$ are each independently ($C_1$–$C_4$)alkyl or are optionally combined with the nitrogen atom to which each is attached to form a ring selected from aziridine, azetidine, pyrrolidine, piperidine, imidazoline, piperazine and morpholine, each of the rings being optionally substituted with from one to three substituents selected from ($C_1$–$C_4$)alkyl, phenyl, phenyl($C_1$–$C_4$)alkyl, hydroxy, hydroxy($C_1$–$C_4$)alkyl, ($C_1$–$C_4$)alkoxy($C_1$–$C_4$)alkyl and di($C_1$–$C_4$)alkylamino($C_1$–$C_4$)alkyl. Still further preferred are those embodiments in which L is selected from —NH—CH(CH$_3$)CH$_2$CH$_2$CH$_2$—, —CH$_2$CH$_2$—, —OCH$_2$CH(OH)CH$_2$—and —NHCH$_2$CH$_2$CH$_2$—; R$^1$ and R$^2$ are each ethyl; and Ar is a substituted phenyl having the formula:

wherein the subscript q is 1 or 2; each R$^5$ is a substituent independently selected from halogen, NO$_2$, CN, CO$_2$R and C(O)R, wherein each R is independently selected from H and (C$_1$–C$_4$)alkyl; and R$^3$ and R$^4$ taken together with the nitrogen atom to which each is attached form a 5- or 6-membered ring selected from pyrrolidine, piperidine and morpholine.

In a group of particularly preferred embodiments, the compounds have the formula:

wherein the subscripts m and n are each independently integers from 1 to 2; R$^1$ and R$^2$ are as defined above for formula I; and R$^3$ and R$^4$ are each independently selected from the group consisting of (C$_1$–C$_4$)alkyl, or when taken together with the nitrogen atom to which each is attached, form a ring selected from the group consisting of aziridine, azetidine, pyrrolidine and piperidine which is optionally substituted with one or two (C$_1$–C$_4$)alkyl groups.

Most preferred are the compounds having the formula:

with R$^1$, R$^2$, R$^3$, R$^4$ and n and m being selected from the preferred groups above. Most preferred are those compounds provided in the Examples.

Within each of the groups of compounds above, evaluation of efficacy can be accomplished by assays to determine whether the compound inhibits the binding of a chemokine to US28 or a suitable US28 fragment.

Preparation of Compounds of Formula I

Compounds useful in the present methods and compositions can be prepared using generally accepted synthetic techniques starting with commercially available materials (e.g., from Aldrich Chemical Co., Milwaukee, Wis., USA or Fluka Chemical Co.).

Scheme I illustrates the preparation of compounds of formula I:

Scheme I

In this scheme, a di-substituted amine (g) is reacted with epichlorohydrin (h) to provide a linking group reagent (i). A suitably substituted aniline (j) is reacted with 1,4-dichlorobutane (k) to form the N-phenyl pyrrolidine compound (l), having a phenolic hydroxy group. Reaction of l with i, under alkylating conditions provides compounds of formula m as one group of compounds of formula I. Other compounds of formula I can be prepared by substitution of various aniline derivatives (j), alkylating agents (k), and di-substituted amines (g). Similarly, epichlorohydrin can be replaced with other groups having suitable functionality to react with a phenolic hydroxy group as well as a di-substituted amine (g).

Following the outline of Scheme I, 2-amino-5-nitrophenol can be treated with 1,4-dichlorobutane to form N-(2-hydroxy-4-nitrophenyl)pyrrolidine (compound I in which the subscript q is 1 and R$^5$ is a nitro group in a position para to the pyrrolidine ring). Alkylation of the phenol with 3-chloro-1-(N,N-diethylamino)-2-propanol provides compound I-a (see Table in Example 3).

C. Assays for Identifying Compounds Which Block Viral Dissemination

Assays are provided herein for identifying a compound capable of blocking CMV dissemination in a host, by determining whether the compound inhibits the binding of a chemokine to US28 or a US28 fragment.

These assays are typically cell-based assays in which a cell which stably expresses US28 is treated with a candidate compound, or more preferably a compound having formula I above and a chemokine in a competitive binding format. Selection of the most potent compounds can be made according to established practices for receptor-ligand competitive binding studies. A variety of other assay formats are also useful in the present invention. For example, substrate-bound or support-bound chemokines (or ligands) can be contacted with a labeled cell or liposome having an associated US28 or US28 fragment A variety of cell lines can be used in this aspect of the invention. In one group of embodiments, the cell line is a mouse cell line. In other embodiments, the cell line is a human or primate cell line (e.g., human foreskin fibroblasts (HFF), human diploid lung fibroblasts (MRC-5 and WI-38), or HUVECs), 293 and COS-7 cells. The cell lines described are transfected with US28 cDNA, typically under the control of a CMV promoter, using conventional methods. The cell are cultured in a suitable buffer (e.g., IMDM-5% FBS, DMEM 10% FCS, HUVEC complete medium, and the like) then centrifuged and resuspended in assay buffer (e.g., HEPES with NaCl, $CaCl_2$, $MgCl_2$, and BSA) to a concentration of from about $5 \times 10^5$ to about $5 \times 10^7$, preferably from about 2 to about $8 \times 10^6$. Aliquots of the cells are then contacted with the candidate compounds and labeled chemokine.

A variety of chemokines can be used in this aspect of the invention, including, for example, fractalkine, RANTES, MCP-3, MIP-1α and MCP-1. Preferably, the labeled chemokine is labeled fractalkine. Additionally, a variety of labels can also be used with the chemokines described above. Typically, the label will be a fluorescence label, a phosphorescence label, a radiolabel, a calorimetric label, or the like. In preferred embodiments the labeled chemokine is a radiolabeled fractalkine, more preferably, $^{125}$I-fractalkine.

After contacting the cells with one or more candidate compounds in the presence of labeled chemokine, the assay mixture is typically incubated for a period of time of from about 1 to about 6 hours at a temperature of from about 1 to about 10° C. Preferably the mixture is incubated for a period of from about 2 to about 4 hours at a temperature of about 4° C. One of skill in the art will understand that a variety of assay conditions can be employed, depending on the cell line used, the concentrations of the compounds and chemokine and the concentration of the cells themselves.

Following incubation the assay wells (for those embodiments carried out on 96-, 384-, 1536-well or larger plates) are typically harvested under vacuum using filter plates, pre-soaked with PEI solution. Scintillation fluid (for radiolabel assays) is added, the plates are sealed and the wells are counted.

D. Compositions Useful in the Treatment of CMV Infection

The present invention also provides compositions useful for preventing CMV dissemination in a host, which comprises a pharmaceutically acceptable carrier or adjuvant and an effective amount of a compound identified using the assays described herein. Preferably, the compound is a compound of formula I.

Typically, the compositions contain from about 0.1% to about 99% by weight of active compound, and preferably from about 10% to about 60% by weight depending on which method of administration is employed.

A CMV dissemination-inhibiting amount is that amount of active compound required to slow the progression of viral dissemination or reduce the amount of viral dissemination from that which would otherwise occur without administration of the compound. Or, it is an amount of active compound required to slow the progression or reduce the intensity of symptoms resulting from CMV infection or reactivation or elimination thereof.

CMV dissemination-inhibiting activity of compounds of the invention can be determined according to the assays described herein. The assays provide an indication of chemokine binding to US28, more typically fractalkine binding to US28. The compounds provided herein inhibit the binding of fractalkine to US28 with activity expressed as IC50 (that amount of compound that reduces fractalkine binding by 50%). The compounds provided herein will typically exhibit an IC50 of approximately 50 μM or less, preferably 25 μM or less, more preferably 10 μM or less, and most preferably less than 1 μM.

For the compositions of the invention, the proportion of each carrier, diluent or adjuvant is determined by the solubility and chemical nature of the compound and the route of administration according to standard pharmaceutical practice. In order to obtain consistency of administration, however, it is preferred that a composition of the invention is in the form of a unit dose. For example, the unit dose presentation forms for oral administration may be tablets and capsules and may contain conventional excipients such as binding agents (e.g., acacia, gelatin, sorbitol, or polyvinylpyrrolidone), fillers (e.g., lactose, sugar, maize-starch, calcium phosphate, sorbitol or glycine), tableting lubricants (e.g., magnesium stearate), disintegrants (e.g., starch, polyvinylpyrrolidone, sodium starch glycoallate or microcrystalline cellulose), or pharmaceutically acceptable wetting agents (e.g., sodium lauryl sulfate).

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 1 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting, or the like. Repeated blending operations may be used to distribute the active agent throughout those compositions employing large quantities of tillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

In another embodiment, the invention provides the subject compounds in the form of a pro-drug, which can be metabolically or chemically converted to the subject compound by the recipient host. A wide variety of pro-drug derivatives are known in the art such as those that rely on hydrolytic cleavage or oxidative activation of the prodrug.

The compositions may be advantageously combined and/or used in combination with other antiviral agents which are either therapeutic or prophylactic agents, and different from the subject compounds. The compositions may also be advantageously combined and/or used in combination with agents that treat or induce conditions often associated with the viral infections that are sensitive to the present compounds, such as anti-HIV agents or immunosuppressive agents. In many instances, administration in conjunction with the subject compositions enhances the efficacy of such agents. Exemplary antiviral agents include ganciclovir, foscamet and cidofovir. Exemplary anti-HIV agents include indinavir, ritonavir, AZT, lamivudine and saquinavir. Exemplary immunosuppressive agents include cyclosporin and FK-506. The compositions may also be advantageously used as antiviral prophylactic treatment in combination with immunosuppressive protocols such as bone-marrow destruction (either by radiation or chemotherapy).

To further assist in understanding the present invention, the following non-limiting examples are provided.

EXAMPLES

Example 1

Radioligand binding assays were carried our in the following manner. The target cells typically used in these assays were either Rhesus dermal fibroblasts which had been infected with Rhesus CMV for 2–4 days, or hUS28 transfected murine cells. Lots of cells verified for fractalkine binding were frozen until use. For the assay, cells were thawed, washed, and resuspended in assay buffer (20 mM HEPES pH 7.1, 140 mM NaCl, 1 mM $CaCl_2$, 5 mM $MgCl_2$, and with 0.2% bovine serum albumin) to a concentration of from $4\times10^5$ to $5\times10^6$ cells/mL. Compounds were prepared as 10×solutions in 20% DMSO, and 0.02 mL was placed in assay plates. Next 0.09 mL of cells was added to the assay plates containing the compounds. Lastly 0.09 mL of $^{125}$I-fractalkine diluted in assay buffer (final concentration ~50 pM, with 20,000–50,000 cpm per well) was added, the plates sealed and incubated for 2–4 hours at 4° C. on a shaker platform. The assay plates were harvested using Packard GF/B filter plates, pre-soaked in 0.3% polyethyleneimmine solution, on a Packard vacuum cell harvester. Scintillation fluid was added to all wells, the plates were sealed and counted in a Top Count scintillation counter. Control wells containing either diluent only (for total counts) or excess unlabeled fractalkine (1 μg/mL, for non-specific binding) were used to calculate the percent of total inhibition. $IC_{50}$ values are those concentrations required to reduce the binding of labeled fractalkine to the receptor by 50%, and were determined by nonlinear regression curve-fitting of the dose-response assays.

Example 2

This example illustrates one method for the preparation of compounds of formula I, from commercially available starting materials.

Synthesis of I-i

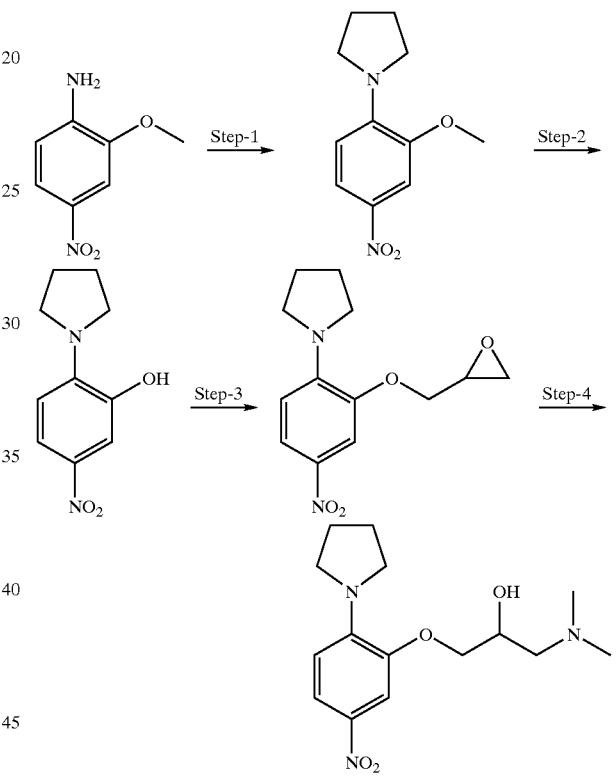

Step-1:

To a oven dry 1 L three-neck round bottom flask, was added NaH (40 g, 1.67 mol), dry DMF (150 mL) and cooled to 0° C. 2-Methoxy-4-nitroaniline (50 g, 0.297 mol) in dry DMF (350 mL) was added over 15 min at 0° C. The reaction mixture was warmed to room temperature and stirring was continued for 1.5 hr. After cooling to 0° C., 1,4-dibromobutane (116 g, 0.54 mol) in dry DMF (150 mL) was added over 15 min and stirring was continued for 15 hr at room temperature. The reaction mixture was poured into ice water, the analytically pure red solid product was filtered and dried under vacuum. Yield: 61 g, 92%.

Step-2:

Dry $K_2CO_3$ (10 g, 0.072 mol) in NMP (60 mL, 0.626 mol) was heated to 165° C. for 1 hr under nitrogen. N-(2-Methoxy-4-nitrophenyl)pyrrolidine (20 g, 0.090 mol) and thiophenol (28 mL, 0.272 mol) were added with stirring at 165° C. Stirring was continued for 2 hr at 150° C. The mixture was cooled to room temperature, neutralized with 1.5 N HCl and extracted with ether. The ether layer was washed with water, brine, dried over Na₂SO₄ and concentrated. The dark red product obtained was purified by column chromatography using petroleum ether-ethylacetate (9:1) as eluent. Yield: 11.5 g, 61%.

Step-3:

N-(2-Hydroxy-4-nitrophenyl)pyrrolidine (5 g, 0.024 mol), racemic-epichlorohydrin (40 mL) and catalytic amount of tetrabutylammonium bromide (60 mg) in 100 mL 3N flask was heated at 50° C. with stirring for 30 min. NaOH (2.3 g, 0.058 mol) in water (5 mL) was added slowly over 15 min. Stirring was continued at 50° C. for 15 hr. Water (100 mL) was added, extracted with chloroform, washed with water, dried over Na₂SO₄ and concentrated. The crude epoxide was purified by column chromatography using 9.5:0.5 petroleum ether:ethylacetate as eluent. Yield: 2.7 g, 43%.

Step-4:

A mixture of the epoxide derivative (200 mg, 0.00075 mol) obtained from the above step and an ethanolic solution of dimethylamine (10 mL, 2.0 M) was stirred at room temperature over night. Solvent was evaporated and the yellow product was purified by column chromatography using chloroform as eluent. Yield: 70 mg, 30.4%.

Synthesis of I-b

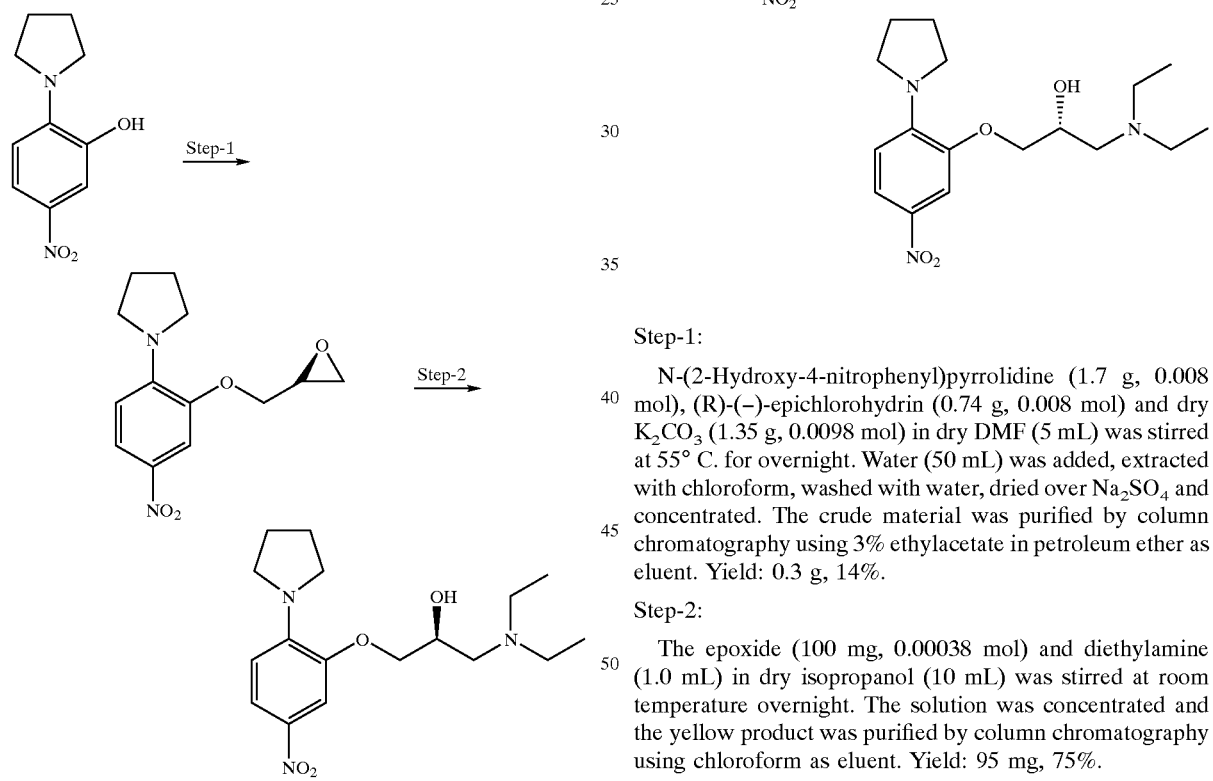

Step-1:

N-(2-Hydroxy-4-nitrophenyl)pyrrolidine (3 g, 0.0144 mol), (S)-(+)-epichlorohydrin (1.4 g, 0.015 mol) and dry K₂CO₃ (2.6 g, 0.0187 mol) in dry acetonitrile (40 mL) was stirred at 60° C. for overnight. Water (100 mL) was added, extracted with chloroform, washed with water, dried over Na₂SO₄ and concentrated. The red crude product was carried on to the next step without purification. Yield: 3.0 g, 78%.

Step-2:

The crude epoxide (100 mg, 0.00038 mol) and diethylamine (3 mL) was stirred at room temperature for overnight. The solution was concentrated and the yellow product was purified by column chromatography using 0.2% methanol in chloroform as eluent. Yield: 60 mg, 47%.

Synthesis of I-l

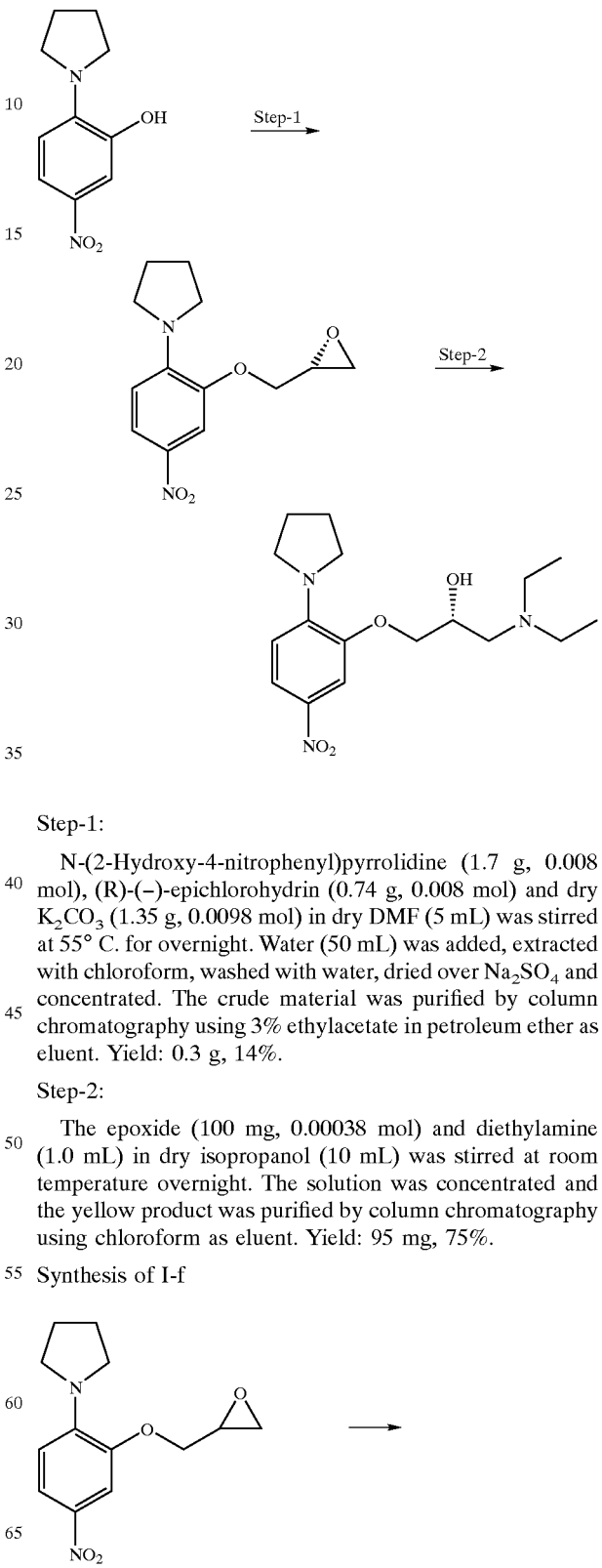

Step-1:

N-(2-Hydroxy-4-nitrophenyl)pyrrolidine (1.7 g, 0.008 mol), (R)-(−)-epichlorohydrin (0.74 g, 0.008 mol) and dry K₂CO₃ (1.35 g, 0.0098 mol) in dry DMF (5 mL) was stirred at 55° C. for overnight. Water (50 mL) was added, extracted with chloroform, washed with water, dried over Na₂SO₄ and concentrated. The crude material was purified by column chromatography using 3% ethylacetate in petroleum ether as eluent. Yield: 0.3 g, 14%.

Step-2:

The epoxide (100 mg, 0.00038 mol) and diethylamine (1.0 mL) in dry isopropanol (10 mL) was stirred at room temperature overnight. The solution was concentrated and the yellow product was purified by column chromatography using chloroform as eluent. Yield: 95 mg, 75%.

Synthesis of I-f

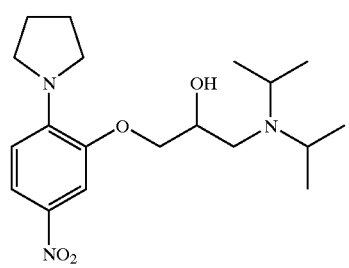

A mixture of the epoxide (100 mg, 0.00038 mol) derivative (obtained from Example 3) and diisopropylamine (2 mL) in isopropanol (5 mL) was stirred at room temperature overnight. The yellow product obtained after the evaporation of the solvent was purified by column chromatography using chloroform as eluent. Yield: 69 mg, 50%.

Example 3

The table below illustrates the activity associated with various compounds prepared by the methods described above and evaluation using the assays also provided above.

| Compound | hUS28 IC$_{50}$ ($\mu$M) |
|---|---|
| 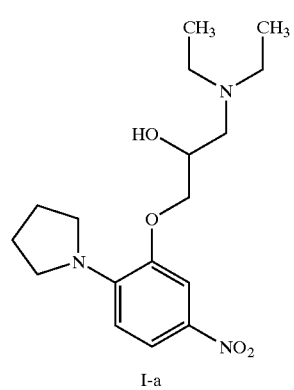<br>I-a | +++ |
| 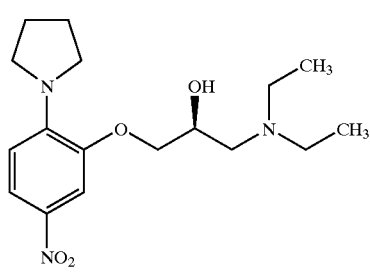<br>I-b | +++ |
| 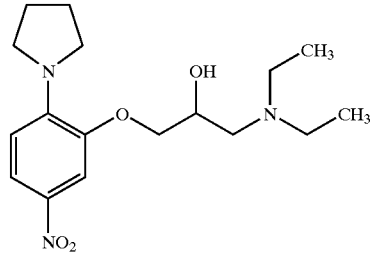<br>I-c | +++ |
| 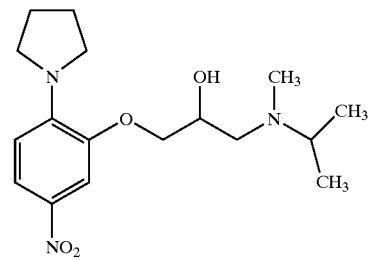<br>I-d | +++ |
| 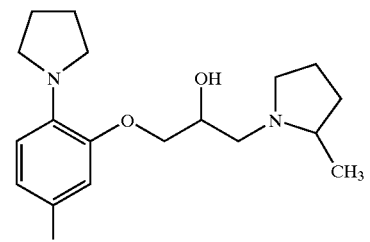<br>I-e | +++ |
| 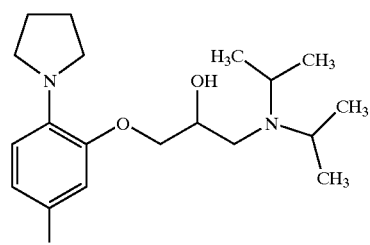<br>I-f | +++ |
| 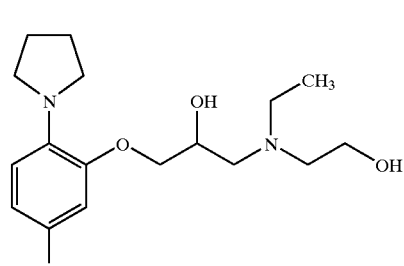<br>I-g | +++ |

-continued
| Compound | hUS28 IC$_{50}$ ($\mu$M) |
|---|---|
| 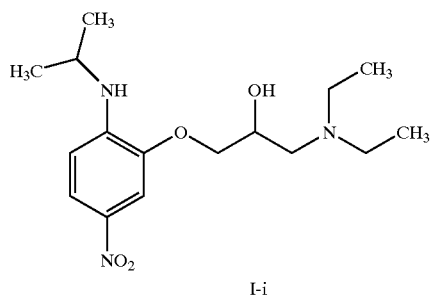 I-h | +++ |
| 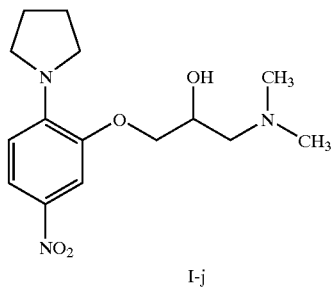 I-i | +++ |
| 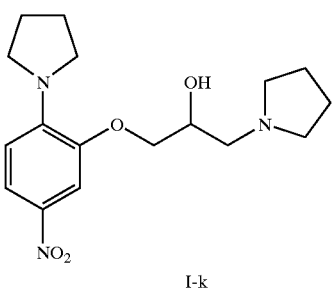 I-j | +++ |
| 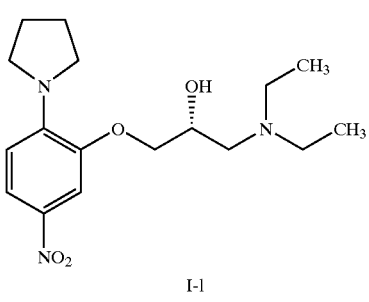 I-k | ++ |
| 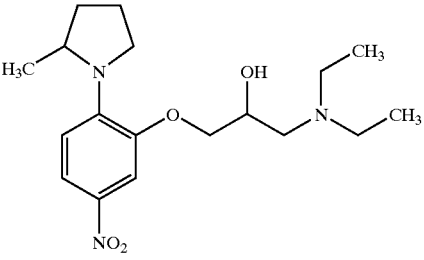 I-l | ++ |
-continued
| Compound | hUS28 IC$_{50}$ ($\mu$M) |
|---|---|
| 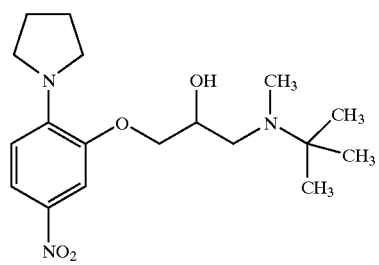 I-m | ++ |
| 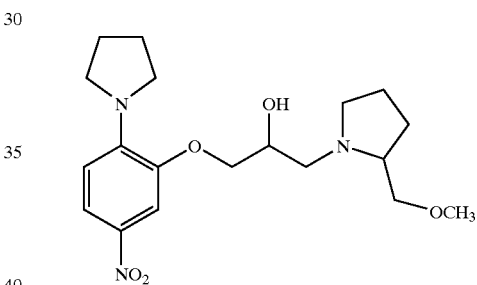 I-n | ++ |
| 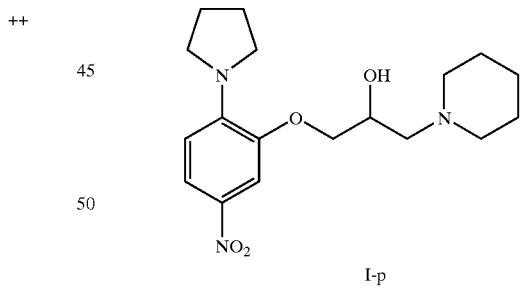 I-o | ++ |
| 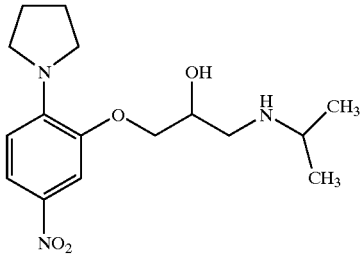 I-p | ++ |
| 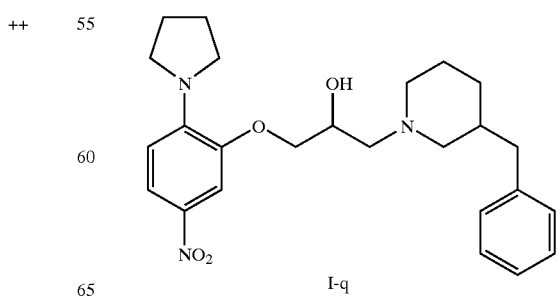 I-q | ++ |

| Compound | hUS28 IC$_{50}$ ($\mu$M) |
|---|---|
| 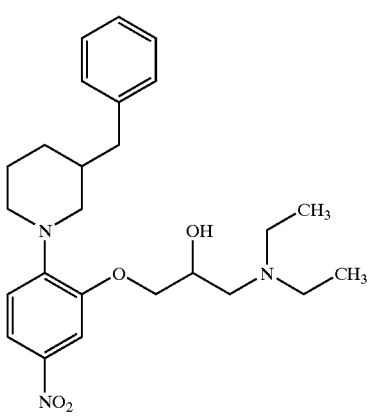 I-r | ++ |
| 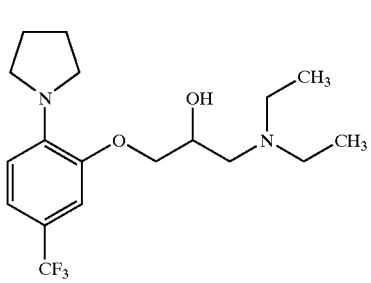 I-s | ++ |
| 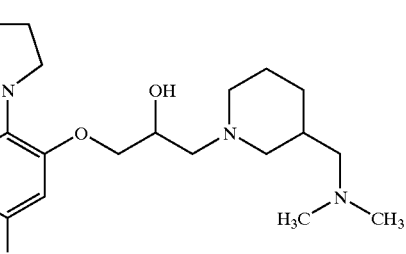 I-t | + |
| 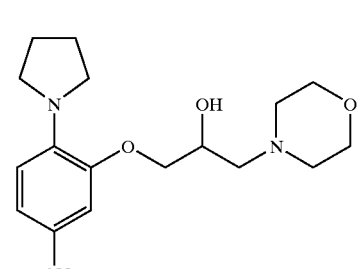 I-u | + |
| 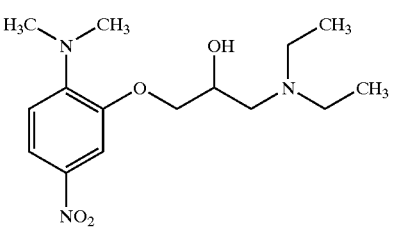 I-v | + |
| 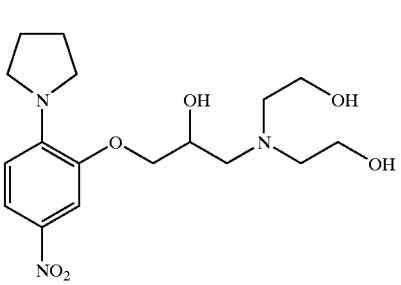 I-w | + |
| 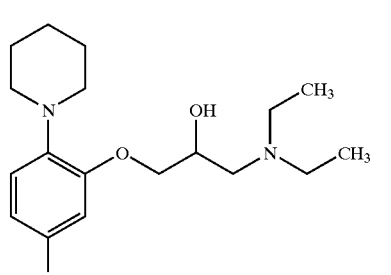 I-x | + |
| 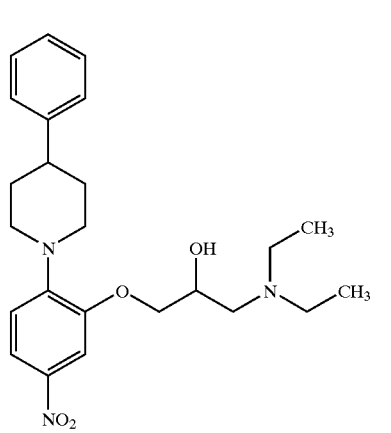 I-y | + |

| Compound | hUS28 IC$_{50}$ ($\mu$M) |
|---|---|
| 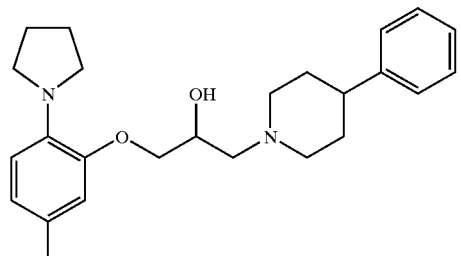 I-z | + |
| 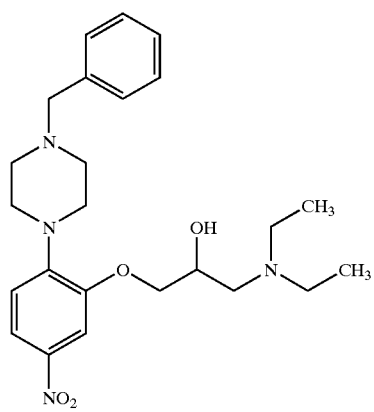 I-aa | + |
| 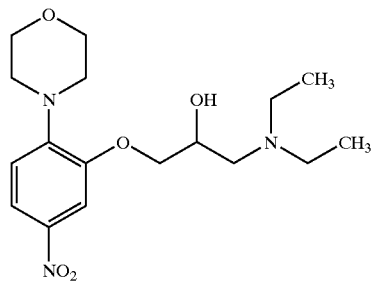 I-ab | + |
| 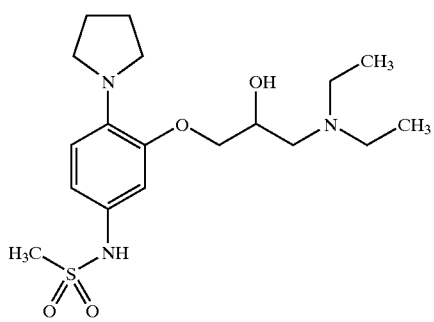 I-ac | + |
| Compound | hUS28 IC$_{50}$ ($\mu$M) |
|---|---|
| 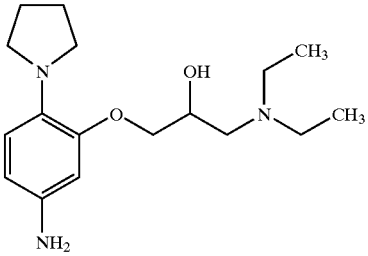 I-ad | + |
| 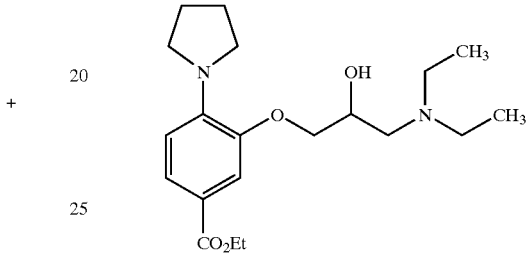 I-ae | + |
| 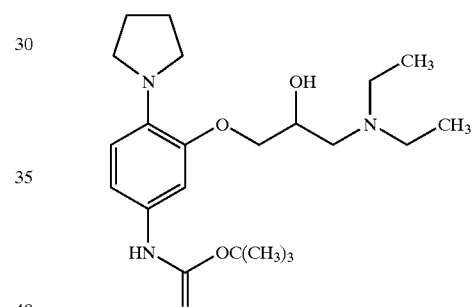 I-af | + |
| 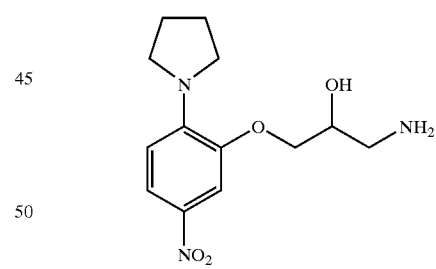 I-ag | + |
| 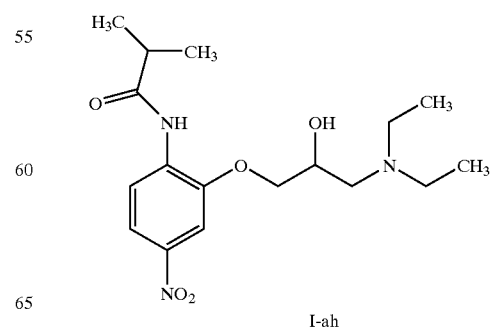 I-ah | + |

-continued

| Compound | hUS28 IC$_{50}$ ($\mu$M) |
|---|---|
| 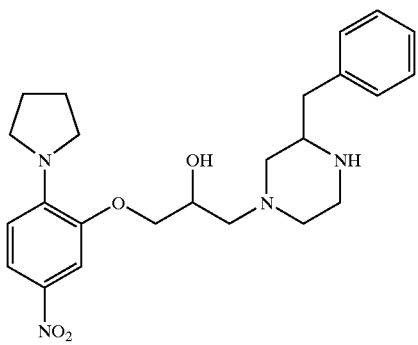<br>I-ai | + |
| 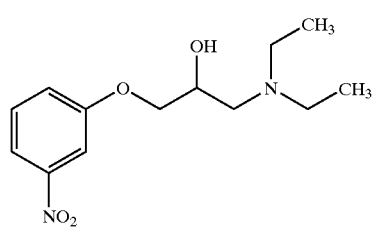<br>I-aj | + |
| 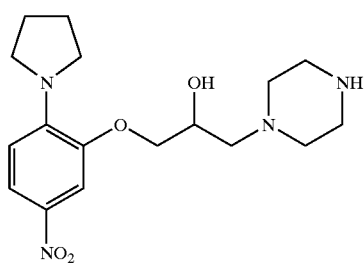<br>I-ak | + |
| 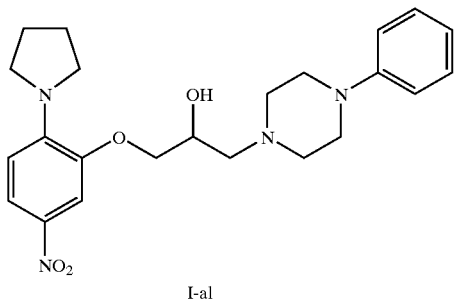<br>I-al | + |
| 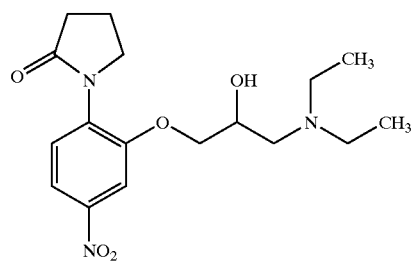<br>I-am | + |

-continued

| Compound | hUS28 IC$_{50}$ ($\mu$M) |
|---|---|
| 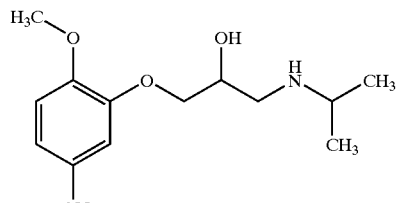<br>I-an | + |
| 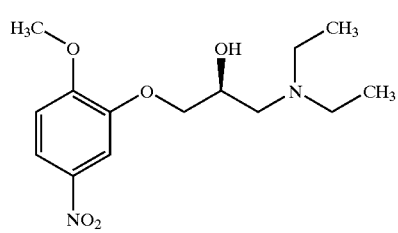<br>I-ao | + |
| 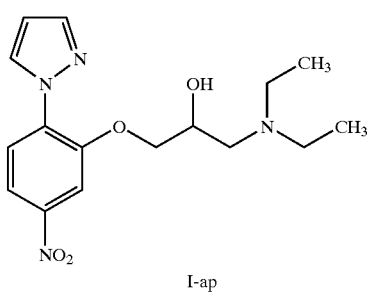<br>I-ap | + |
| 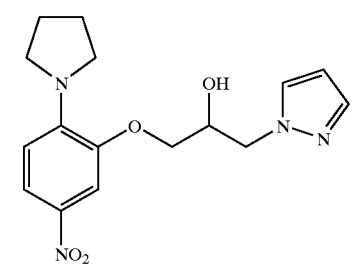<br>I-aq | + | hUS28:
+, 10–40 micromolar;
++, 1–10 micromolar;
+++, less than 1 micromolar

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A pharmaceutical composition comprising a pharmaceutically acceptable excipient and a compound having the formula:

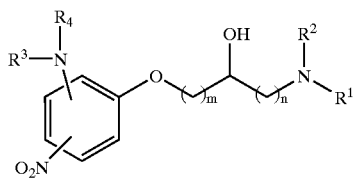

or a pharmaceutically acceptable salt of the compound, wherein the subscripts m and n are each independently integers from 1 to 2;

$R^1$ and $R^2$ are each independently selected from the group consisting of $(C_1-C_4)$alkyl, wherein the alkyl portions are optionally substituted with OH or $(C_1-C_4)$alkoxy groups; or $R^1$ and $R^2$ are optionally combined with the nitrogen atom to which each is attached to form a ring selected from the group consisting of aziridine, azetidine, pyrrolidine, piperidine, imidazoline, piperazine and morpholine, each of said rings being optionally substituted with from one to three substituents selected from the group consisting of $(C_1-C_4)$alkyl, phenyl, phenyl$(C_1-C_4)$alkyl, hydroxy, hydroxy$(C_1-C_4)$alkyl, $(C_1-C_4)$alkoxy$(C_1-C_4)$alkyl and di$(C_1-C_4)$alkylanxino$(C_1-C_4)$alkyl; and $R^3$ and $R^4$ are each independently selected from the group consisting of $(C_1-C_4)$alkyl, or when taken together with the nitrogen atom to which each is attached, form a ring selected from the group consisting of aziridine, azetidine, pyrrolidine and piperidine which is optionally substituted with one or two $(C_1-C_4)$alkyl groups; and wherein the pharmaceutical composition is formulated as an oral, topical, parenteral. or rectal preparation, or as an intraocular implant.

2. A pharmaceutical composition of claim 1, wherein m and n are each 1; $R^1$ and $R^2$ are each ethyl; $R^3$ and $R^4$ are combined with the nitrogen atom to which each is attached to form a pyrrolidine ring; and wherein said compound has the R-stereochemistry at the carbon bearing the hydroxy group.

3. A pharmaceutical composition of claim 1, wherein m and n are each 1; $R^1$ and $R^2$ are each ethyl; $R^3$ and $R^4$ are combined with the nitrogen atom to which each is attached to form a pyrrolidine ring; and wherein said compound has the S-stereochemistry at the carbon bearing the hydroxy group.

4. A pharmaceutical composition of claim 1, wherein the pharmaceutically acceptable excipient is a binding agent, a filler, a tableting lubricant, a disintegrant, or wetting agent.

5. A pharmaceutical composition of claim 4, wherein said composition is in unit dose format.

6. A pharmaceutical composition of claim 5, wherein the composition is an oral administration formulation.

7. A pharmaceutical composition of claim 4, wherein the composition is in a parenteral administration formulation.

8. A pharmaceutical composition of claim 4, wherein the composition is in the form of a capsule, caplet, lozenge, powder, tablet, or granule.

9. A pharmaceutical composition of claim 1, wherein the compound is an inhibitor of fractalkine binding to the US28 receptor.

10. A pharmaceutical composition of claim 1, wherein the compound has an $IC_{50}$ of about 50 micromolar or less for inhibiting the binding of fractalkine to the US28 receptor.

11. A pharmaceutical composition of claim 1, wherein the composition is in a topical application formulation.

12. A phannaceutical composition of claim 1, wherein the composition is in a formulation for rectal application.

* * * * *